United States Patent

Abrams et al.

[11] Patent Number: 6,142,146
[45] Date of Patent: Nov. 7, 2000

[54] INHALATION DEVICE

[75] Inventors: Andrew L. Abrams, Westport, Conn.; Anand V. Gumaste, Robbinsville, N.J.

[73] Assignee: Microdose Technologies, Inc., Monmouth Jct., N.J.

[21] Appl. No.: 09/097,105

[22] Filed: Jun. 12, 1998

[51] Int. Cl.[7] ............................................. A61M 15/00
[52] U.S. Cl. ................................................. 128/203.15
[58] Field of Search ..................... 128/200.16, 203.15, 128/203.21, 200.14; 604/58

[56] References Cited

U.S. PATENT DOCUMENTS

| | | | |
|---|---|---|---|
| 2,517,482 | 8/1950 | Hall | 128/206 |
| 3,507,277 | 4/1970 | Altounyan et al. | 128/208 |
| 3,518,992 | 7/1970 | Altounyan et al. | 128/208 |
| 3,635,219 | 1/1972 | Altounyan et al. | 128/266 |
| 3,795,244 | 3/1974 | Lax et al. | 128/266 |
| 3,807,400 | 4/1974 | Cocozza | 128/266 |
| 3,828,773 | 8/1974 | Buch et al. | 128/200.16 |
| 3,831,606 | 8/1974 | Damani et al. | 128/266 |
| 3,948,264 | 4/1976 | Wilke et al. | 128/266 |
| 3,957,965 | 5/1976 | Hartley et al. | 424/14 |
| 4,001,650 | 1/1977 | Romain | 128/200.16 |
| 4,319,155 | 3/1982 | Nakai et al. | 128/200.16 |
| 4,334,531 | 6/1982 | Reichl et al. | 128/200.14 |
| 4,349,531 | 9/1982 | Mlodozeniec et al. | 424/27 |
| 4,915,008 | 4/1990 | Sakashita | 84/735 |
| 4,996,502 | 2/1991 | Endo | 128/200.16 |
| 5,069,107 | 12/1991 | Sakashita | 84/659 |
| 5,152,456 | 10/1992 | Ross et al. | 128/200.16 |
| 5,195,528 | 3/1993 | Hok | 128/716 |
| 5,267,555 | 12/1993 | Pajalich | 128/200.14 |
| 5,284,133 | 2/1994 | Burns et al. | 128/200.23 |
| 5,312,281 | 5/1994 | Talajasjo et al. | 446/25 |
| 5,331,953 | 7/1994 | Andersson et al. | 128/203.15 |
| 5,349,947 | 9/1994 | Newhouse et al. | 128/203.21 |
| 5,363,842 | 11/1994 | Mishelevich et al. | 128/200.14 |
| 5,369,977 | 12/1994 | Rhodes et al. | 73/23.3 |
| 5,372,128 | 12/1994 | Haber et al. | 128/203.21 |
| 5,383,469 | 1/1995 | Vreman et al. | 128/719 |
| 5,437,271 | 8/1995 | Hodson et al. | 128/203.21 |
| 5,452,711 | 9/1995 | Gault | 128/200.14 |
| 5,458,135 | 10/1995 | Patton et al. | 128/200.14 |
| 5,459,280 | 10/1995 | Masuda et al. | 84/622 |
| 5,469,843 | 11/1995 | Hodson | 128/203.15 |
| 5,476,093 | 12/1995 | Lankinen | 128/203.15 |
| 5,505,195 | 4/1996 | Wolf et al. | 128/203.15 |
| 5,522,383 | 6/1996 | Calvert et al. | 128/203.15 |
| 5,551,416 | 9/1996 | Stimpson et al. | 128/200.16 |
| 5,655,523 | 8/1997 | Hodson et al. | 128/203.15 |
| 5,676,130 | 10/1997 | Gupte et al. | 128/203.15 |
| 5,694,920 | 12/1997 | Abrams et al. | 128/200.16 |
| 5,699,649 | 12/1997 | Abrams et al. | 53/428 |
| 5,714,007 | 2/1998 | Pletcher et al. | 118/629 |
| 5,724,959 | 3/1998 | McAughey et al. | 128/203.15 |
| 5,735,263 | 4/1998 | Rubsamen et al. | 128/200.14 |
| 5,829,434 | 11/1998 | Ambrosio et al. | 128/203.15 |
| 5,839,429 | 11/1998 | Marnfeldt et al. | 128/203.15 |

FOREIGN PATENT DOCUMENTS

| | | |
|---|---|---|
| 0174033 | 3/1986 | European Pat. Off. . |
| 0506293 | 3/1992 | European Pat. Off. . |
| 2605249 | 10/1986 | France . |
| 2072536 | 10/1981 | United Kingdom . |
| 2262452 | 6/1993 | United Kingdom . |
| 9013327 | 11/1990 | WIPO . |
| 9013328 | 11/1990 | WIPO . |
| 9419042 | 9/1994 | WIPO . |
| 9726934 | 7/1997 | WIPO . |
| WO 97/26934 | 7/1997 | WIPO . |
| WO 98/20861 | 5/1998 | WIPO . |

*Primary Examiner*—Aaron J. Lewis
*Attorney, Agent, or Firm*—Hayes, Soloway, Hennessey, Grossman & Hage, P.C.

[57] ABSTRACT

A dry powder inhaler comprises a first chamber in which a dry powder may be deaggregated by a vibrator and separated by size, and a second chamber in which the size-separated deaggregated powder may be picked up by an air stream and carried for introduction into a patient. Electronic circuitry is included for controlling dosing.

54 Claims, 10 Drawing Sheets

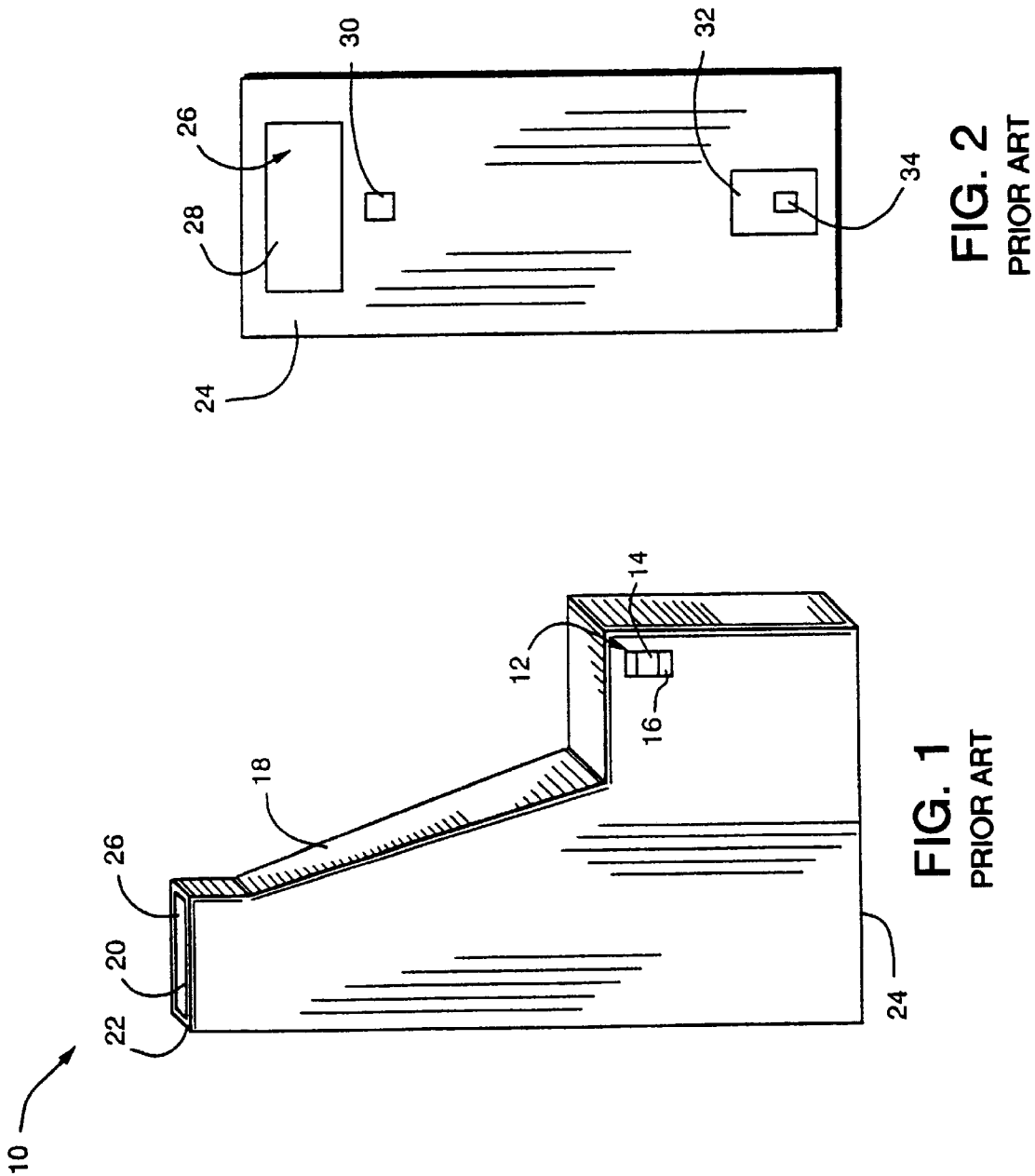

INHALATION DEVICE

BACKGROUND OF THE INVENTION

1. Field of the Invention

The present invention relates generally to the field of inhalation devices, and more specifically, to inhalation devices that utilize vibration to facilitate suspension of powder (e.g., powdered medication) into an inhaled gas stream (e.g., of inhaled air). Particular utility for the present invention is found in the area of facilitating inhalation of powdered medications, although other utilities are contemplated, including other medicament applications.

2. Description of the Prior Art

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drag is optimum when the drug particles delivered to the respiratory tract are between 1 to 5 microns in size. When the drug particles need to be in this size range the dry powder delivery system needs to address a number of issues:

(1) Small size particles develop an electrostatic charge on themselves during manufacturing and storage. This causes the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms. For example, albuterol, in the case of a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air-stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages which are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament. Also, such prior art devices result in uncontrolled amounts or clumps, of powdered material being inhaled into the user's mouth, rather than a constant inhalation of controlled amounts of finely dispersed powder.

The above description of the prior art is taken largely from U.S. Pat. No. 3,948,264 to Wilke et al, who disclose a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electro-mechanical vibrator, the powdered drug many be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule. The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through outlet channel 3 and concurrent pressing of switch 10d to activate the electromechanical vibrating means 10, air is sucked through inlet channels 4 and 12 and the air stream through the secondary inlet channel 4 raises the capsule up against the vibrating plunger rod 10a. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) The air stream through inlet channel 4 and 12 aids in withdrawal of powder from the capsule and carries this powder through the outlet channel 3 to the mouth of the user." (Wilke et al, column 3, lines 45–55). Wilke et al further discloses that the electromechanical vibrator means may be placed at a right angle to the inlet chamber and that the amplitude and frequency of vibration may be altered to regulate dispensing characteristics of the inhaler.

Thus, as noted above, the vibrator in Wilke et al's disclosed inhaler is an electromechanical device consisting of a rod driven by a solenoid buzzer. (This electromechanical means may be a motor driving a cam [Col. 4, Line 40]). A disadvantage of the inhaler implementation as disclosed by Wilke is the relatively large mechanical movement required of the rod to effectively vibrate the capsule. The large movement of the rod, usually around 100s of microns, is necessary due to the elasticity of the capsule walls and inertia of the drug and capsule.

Moreover, solenoid buzzers typically have operating frequencies less than 5 Khz. This operating frequency tends to be noisy and therefore is not desirable when incorporated into a dry powder inhaler from a patient's perspective. A further disadvantage of the electrochemical actuators of Wilke is the requirement for a high energy source (Wilke et al, Col. 3, line 38), thus requiring a large battery source or frequent changes of the battery pack for portable units. Both these features are not desirable from a patient safety and "ease of use" standpoint.

The inhaler of Wilke et al is primarily intended to reduce the amount of powder left behind in the capsule relative to other inhalers cited in the patent disclosure. (Wilke et al, Col. 4, lines 59–68, Col. 5, lines 1–48). However, Wilke et al does not address the need to deaggregate the powder into particle sizes or groups less than 6 microns in size as is required for effective delivery of the medication to the lungs; rather Wilke et al, like the prior art inhalers continues to rely on the air stream velocity to deaggregate the powder ejected into the air stream, into particle sizes suitable for delivery to the lungs.

Another prior art inhalation device is disclosed in Burns et al U.S. Pat. No. 5,284,133. In this device, a liquid medication is atomized by an ultrasonic device such as a piezo element (Burns et al, Col. 10, lines 36–51). A stream of air, usually at a high velocity, or a propellant then carries the atomized particles to the patient. The energy required to atomize the liquid medication in the nebulizer is prohibitively high, making this approach for the delivery of drugs to the lungs only feasible as a desk top unit. The high voltage requirements to drive the piezo, to produce the necessary mechanical displacements, also severely effects the weight and size of the device. It is also not obvious that the nebulizer operating principles can be applied to the dry powder inhalers for delivery or powder medication to the lungs.

The prior art devices therefore have a number of disadvantages which makes them less than desirable for the delivery of dry powder to the lungs. Some of these disadvantages are:

The performance of the prior art inhalers depends on the flowrate generated by the user. Lower flowrate does not result in the powder being totally deaggregated and hence adversely affects the dose delivered to the patient.

Inconsistency in the bioavailability of the drugs from dose-to-dose because of lack of consistency in the deaggregation process.

Large energy requirements for driving the electromechanical based inhalers which increases the size of the devices making them unsuitable for portable use.

In our prior U.S. Pat. No. 5,694,920, issued Dec. 9, 1997, we provide an inhaler that utilizes vibration to facilitate suspension of powder into a gas that overcomes the aforesaid and other disadvantages and drawbacks of the above prior art. More particularly, the inhaler of our aforesaid patent includes a piezoelectric vibrator for vibrating the powder. A controller is provided for controlling supply (i.e., amplitude and/or frequency) of actuating electricity to the vibrator so as to cause vibration of the powder that is adapted to optimally suspend at least a portion of the powder into the gas. As described in our aforesaid patent, the controller may include a user-actuable control for permitting the user to select the vibration frequencies and/or amplitudes for optimally suspending in the gas the type of powder currently being used in the inhaler. The user-actuable control is pre-calibrated with the controller to cause the controller to adjust the frequency and/or amplitude of actuating electricity supplied to the vibrator to be that necessary for vibrating the type of powder selected by the user-actuable control in such a way as to optimally suspend at least a portion of the powder into the gas. The user-actuable control may include selection gradations in terms of the average size of the powder particles to be suspended in the gas, and/or in terms of desired vibration frequencies and amplitudes. Vibration frequency would be adjusted to at least about 12 KHz, in order to optimally suspend such commonly used powdered medications in the gas. Of course, vibration frequency and amplitude may be adjusted to optimize suspension of the powdered medication being used.

An electrostatic field that is established across the air stream, whereby by controlling the strength of the electrostatic field primarily only particle sizes of interest are introduced into the air stream, while larger size particles are left behind in the container. This reduces the inconsistency associated with the bioavailability of the drug because of the large particles being deposited into the mouth or throat as is common with devices described in prior art.

SUMMARY OF THE INVENTION

The present invention provides an improvement over prior art inhalation devices such as described in our aforesaid U.S. Pat. No. 5,694,920. In one embodiment of the invention, the inhaler contains two or more vibrator means or piezoelectric elements so that different drugs, i.e. of different particle size, may be delivered from the same inhaler.

In yet another embodiment of the invention, the piezoelectric elements are switched between two or more set frequencies, or frequencies swept so as to avoid potentially setting up standing waves in the powder.

In yet another embodiment of the invention, the inhaler includes electronic circuitry for recording and/or controlling one or more functions such as dose counting, patient compliance monitoring, and patient compliance reminders. Also, the inhaler may be programmed according to a delivery protocol, i.e. to alter the quantity of drug delivered over time. If desired, the inhaler also may include an environmental sensor and knockout control, for example, to deactivate the inhaler in the event it is inadvertently exposed to too high a temperature, a clock to deactivate the inhaler in the event its shelf life is exceeded, and/or a security/safety lock-out.

BRIEF DESCRIPTION OF THE DRAWINGS

Still other features and advantages of the present invention may be seen from the following detailed description, taken in connection with the attached drawings, wherein like numerals depict like parts, and wherein:

FIG. 1 is a perspective view of an inhaler of the prior art;

FIG. 2 is a rear plane view of the inhaler shown in FIG. 1;

DETAILED DESCRIPTION OF PREFERRED EMBODIMENTS

Figure 3:
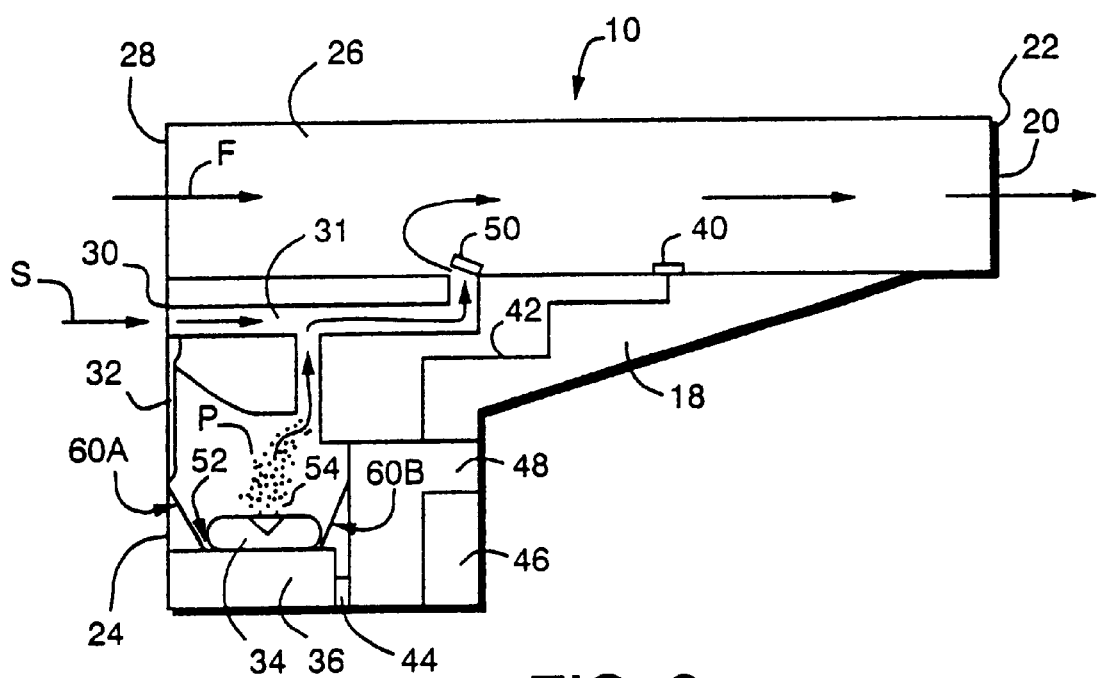
FIG. 3 is a longitudinal cross-sectional schematic view of the inhaler of FIG. 1.

FIGS. 1–3 illustrate an embodiment 10 of inhaler made in accordance with our aforesaid U.S. Pat. No. 5,694,920. Inhaler 10 includes a hard plastic or metal housing 18 having a generally L-shaped longitudinal cross-section. Housing 18 includes four air flow openings 20, 28, 30, and 32. Inhaler 10 includes a main air flow passage 26 which extends the length of the housing 18 from the front 22 (at opening 20) to the rear 24 thereof (at opening 28) and has a generally square-shaped transverse cross-section, so as to permit air flow therethrough (denoted by arrow F in FIG. 1).

Secondary air conduit 31 is generally L-shaped and runs longitudinally from opening 30 in the rear 24 surface of the housing 18 to main passage 26. One-way flow valve 50 is mounted to the inner surface 33 of the main passage 26 via a conventional spring-biased hinge mechanism (not shown), which is adapted to cause the valve 50 to completely block air flow S through the conduit 31 to the main passage 26 when the pressure of the air flow F in the main passage 26 is below a predetermined threshold indicative of inhalation through the passage 26 by a user.

Figure 4:
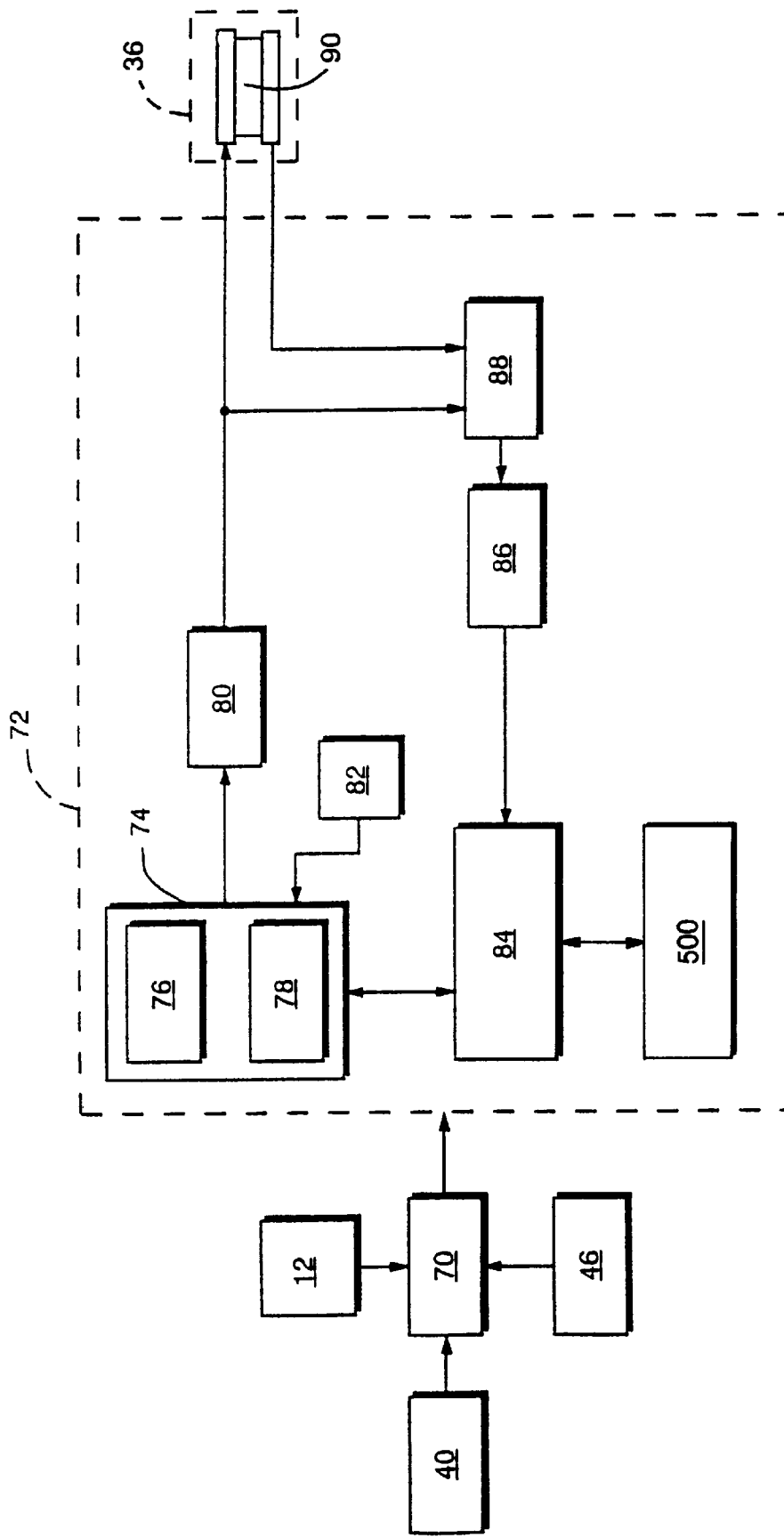
FIG. 4 is a functional block diagram of the vibration control system of one embodiment of FIG. 1.

Powder dispensing chamber 54 is formed in housing 18 for holding a capsule 34 of powder medication to be inhaled. Housing 18 includes a moveable panel portion 32 in the rear 24 for permitting the capsule 34 to be introduced into the chamber 54 and placed on the seating 52 of vibration means 36 between guiding means 60A, 60B. Preferably, means 36 comprises a hard plastic or metallic protective shell 37 enclosing a piezoelectric vibrator 90. (FIG. 4). Preferably, vibrator 90 is mechanically coupled through the shell 37 via a disk (not shown) to the drug cartridge 34 so as to permit maximum vibratory energy to be transmitted from the vibrator 90 through the shell 37 to the cartridge 34. Guiding means 60A, 60B includes two surfaces which slant downwardly toward the seating 52 so as to permit easy introduction and retention of the capsule on the seating 52 in the chamber 51. Removable panel 32 includes another air inlet 34 for permitting additional air flow S2 from the chamber 51 through conduit 61 into conduit 31 during inhalation by the user. Preferably, panel 32 and housing 18 include conventional mating mounting means (not shown) for permitting the panel 32 to be removably resecurable to the housing by the user between introduction of fresh (i.e., completely full) capsules and removal of spent (i.e., empty) capsules.

Inhaler 10 also includes a conventional miniature air stream velocity or pressure sensor 40 mounted on the inner surface of the conduit 26 so as to sense the speed and/or pressure of the air stream F. Preferably, sensor 40 comprises a conventional spring-loaded flapper-yield switch which generates electronic signals indicative of the speed and/or pressure of the air stream F in the conduit 26, and transmits those signals via electrical connection 42 to electronic control circuitry 48 contained in housing 18 for controlling actuation of the vibrator means based upon those signals.

Preferably, the control circuitry 48 is embodied as an application specific integrated circuit chip and/or some other type of very highly integrated circuit chip. Alternatively, control circuitry 48 may take the form of a microprocessor, or discrete electrical and electronic components. As will be described more fully below, the control circuitry 48 determines the amplitude and frequency of actuating power to be supplied from conventional power source 46 (e.g., one or more D.C. batteries) to the piezoelectric vibrator to thereby control vibration of the vibrator. The actuating power is supplied to the piezoelectric element 90 via electrical connection 44 between the vibrator and the circuitry 48.

Piezoelectric element 90 is made of a material that has a high-frequency, and preferably; ultrasonic resonant vibratory frequency (e.g., about 15 to 100 MHz), and is caused to vibrate with a particular frequency and amplitude depending upon the frequency and/or amplitude of excitation electricity applied to the piezoelectric element 90. Examples of materials that can be used to comprise the piezoelectric element 90 include quartz and polycrystalline ceramic materials (e.g., barium titanate and lead zirconate titanate). Advantageously, by vibrating the piezoelectric element 90 at ultrasonic frequencies, the noise associated with vibrating the piezoelectric element 90 at lower (i.e., non-ultrasonic) frequencies can be avoided.

Turning specifically to FIG. 4, the various functional components and operation of the control circuitry 48 will now be described. As will be understood by those skilled in the art, although the functional components shown in FIG. 4 are directed to an analog realization of the control circuitry 48, the components of FIG. 4 could be appropriately modified to realize control circuitry 48 in a digital embodiment without departing from this embodiment 10 of the present invention.

Control circuitry 48 preferably includes actuation controller 70 and vibratory feedback control system 72. Acutation controller 70 comprises a conventional switching mechanism for permitting actuating power to be supplied from the power source 46 to the control system 72 depending upon the signals supplied to it from sensor 40 and the state of the power switch 12. In other words, controller 70 permits actuating power to be supplied from the source 46 to the system 72 when the sliding indicator bar 14 of switch 12 is set to the "ON" position in channel track 16 and the inhalation sensor 40 supplies signals to the controller 70 that indicate that the inhalation is occurring through the main passage 26. However, controller 70 does not permit actuating power to flow from the source to the system 72 when either the switch 12 is set to "OFF" or the signals supplied to the controller 70 from the sensor 40 indicate that inhalation is not taking place through the conduit 26.

When controller 70 first permits actuating power to be supplied from the source 46 to the feedback control system 72, the system 72 enters an initialization state wherein controllable means for supplying a predetermined frequency and amplitude of actuating electricity 74 is caused to generate control signals for causing conventional pump circuit 80 to generate an initial desired frequency and amplitude of actuating electricity based upon stored values thereof stored in the initialization memory means 82. Preferably, means 74 comprises conventional frequency sweep generator and frequency generator means 76 and 78, respectively. The signals generated by means 74 are then supplied to charge pump circuit 80 to cause circuit 80 to supply the piezoelectric element 90 with actuating electricity specified by the signals.

Preferably, the initial frequency and amplitude of actuating electricity supplied to the piezoelectric element 90 is pre-calibrated to cause the piezoelectric element 90 to vibrate at its resonance frequency when no powder cartridge or powder is placed on the means 36. As will be appreciated by those skilled in the art, maximum transfer of vibratory power from the piezoelectric element to the powder in the container 34 takes place when the piezoelectric element vibrates at its resonant frequency. It has been found that this results in maximum deaggregation and suspension of the powder from the container 34 into the air to be inhaled by the user. However, when the container 36 or powder is placed on the vibrator means 36, the weight and volume of the powder container, and the weight, volume, and particular size of the powder to be suspended by the piezoelectric element can change the vibration characteristics of the piezoelectric element, and cause the piezoelectric element to vibrate at other than its resonant frequency. This can result in reduced vibratory energy transfer to the powder from the piezoelectric element, and thereby, lessen the efficiency of the piezoelectric element in deaggregating and suspending the powder in the air inhaled by the user.

The feedback control system 72 overcomes this problem. In control system 72, after the initial frequency and amplitude of actuating electricity are supplied to the piezoelectric element 90, the frequency generating means 74 systematically generates control signals indicative of many different amplitudes and frequencies of electricity for being supplied to the piezoelectric element 90 by the circuit 80. As the generating means 74 "cycles through" the different frequencies and amplitudes, the instantaneous power transfer characteristics of the piezoelectric element 90 for each of these different frequencies and amplitudes are determined by the detector 88, which transmits this information to the peak power detector 86. Peak detector 86 analyzes the instantaneous power transfer characteristics of the piezoelectric element 90 and signals the sample and hold feedback controller 84 when the power transfer characteristics are at local maxima. The controller 84 correlates these local maxima with the frequencies and amplitudes commanded by the generator 74 to be supplied to the piezoelectric element 90.

After the frequency generator 74 has finished its sweep through the frequencies and amplitudes of power supplied to the piezoelectric element 90, the controller 84 causes the generator 74 to cycle through the frequencies and amplitudes of power that resulted in local maxima, and then determines which of these frequencies and amplitudes results in optimal power transfer characteristics through the piezoelectric element 90.

Completing the controller 72 is a clock 500 which is tripped when actuating electricity is first supplied to the piezoelectric element 90. Clock 500 includes a counter which prevents a second activation of the piezoelectric element for a preset period of time. Thus, overuse and overdosing by the patient are prevented.

In operation of embodiment 10, the drug-containing package 34 is punctured and inserted onto the surface 52 of vibrator 36 in chamber 51 in the manner described previously. The power switch is placed in the "ON" position and the user inhales air through the conduit 26, air flow F is generated through conduit 26. This causes one-way valve 50 to deflect to admit air flow S through opening 30 into conduit 26, and also causes air flow S2 through opening 34 and chamber 51 into conduit 26. The inhalation of air stream F is sensed by sensor 40 and is signaled to actuation controller 70, which causes power to be supplied to the controller 72. The controller 72 then adjusts the amplitude and frequency of actuating power supplied to the piezoelectric element until they are optimized for the best possible de-aggregation and suspension of the powder P from the capsule into the air stream F via air flows S and S2.

Figure 5:
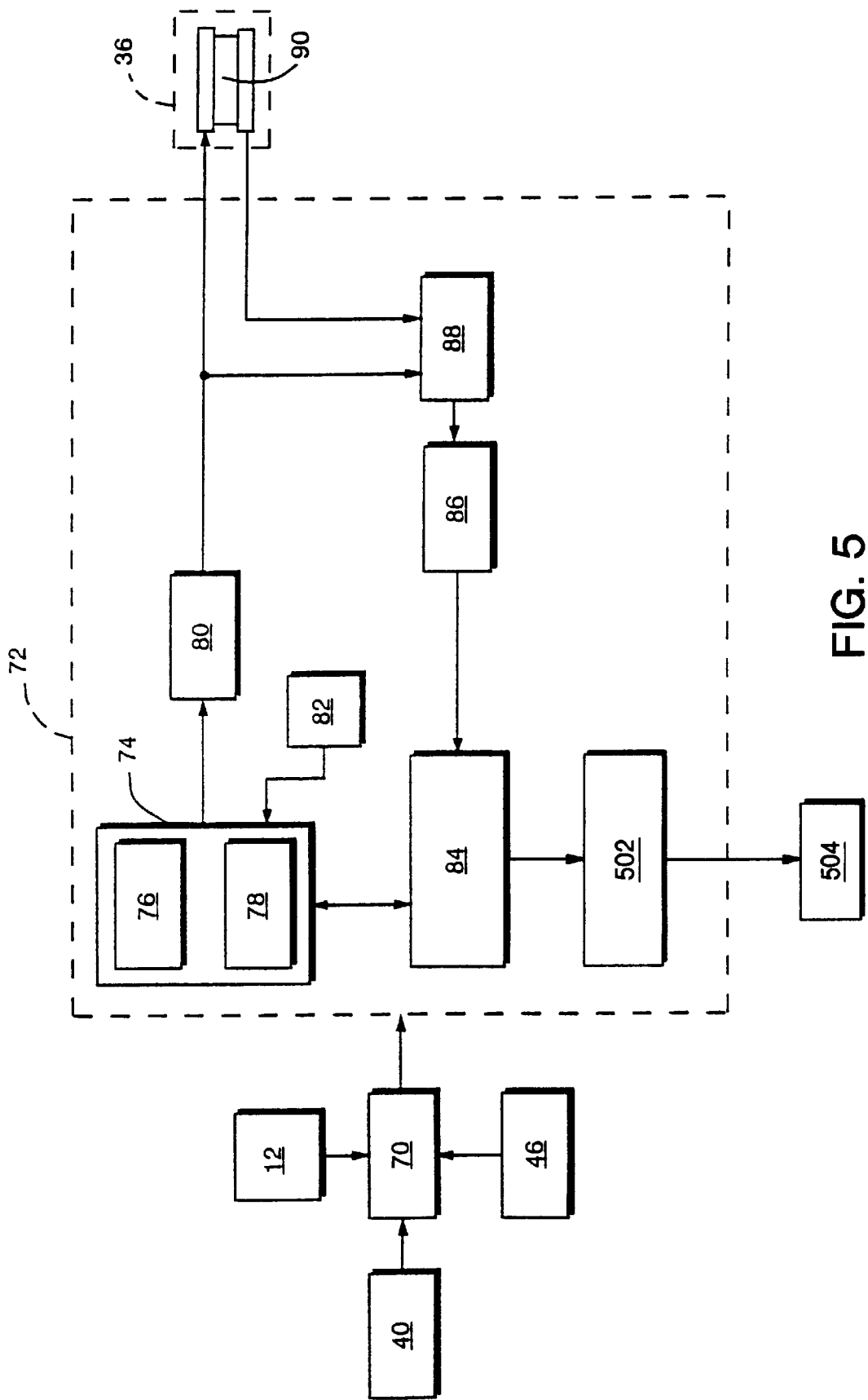
FIG. 5 is a functional block diagram of the vibration control system of another embodiment of the invention.

FIG. 5 illustrates another embodiment of the invention. FIG. 5 is similar to FIG. 4, except the clock 500 is replaced with a counter 502 which counts the number of doses delivered by the device. Counter 502 is connected to a display 504 which displays the number of doses delivered, or, optionally, the number of doses remaining.

Figure 6:
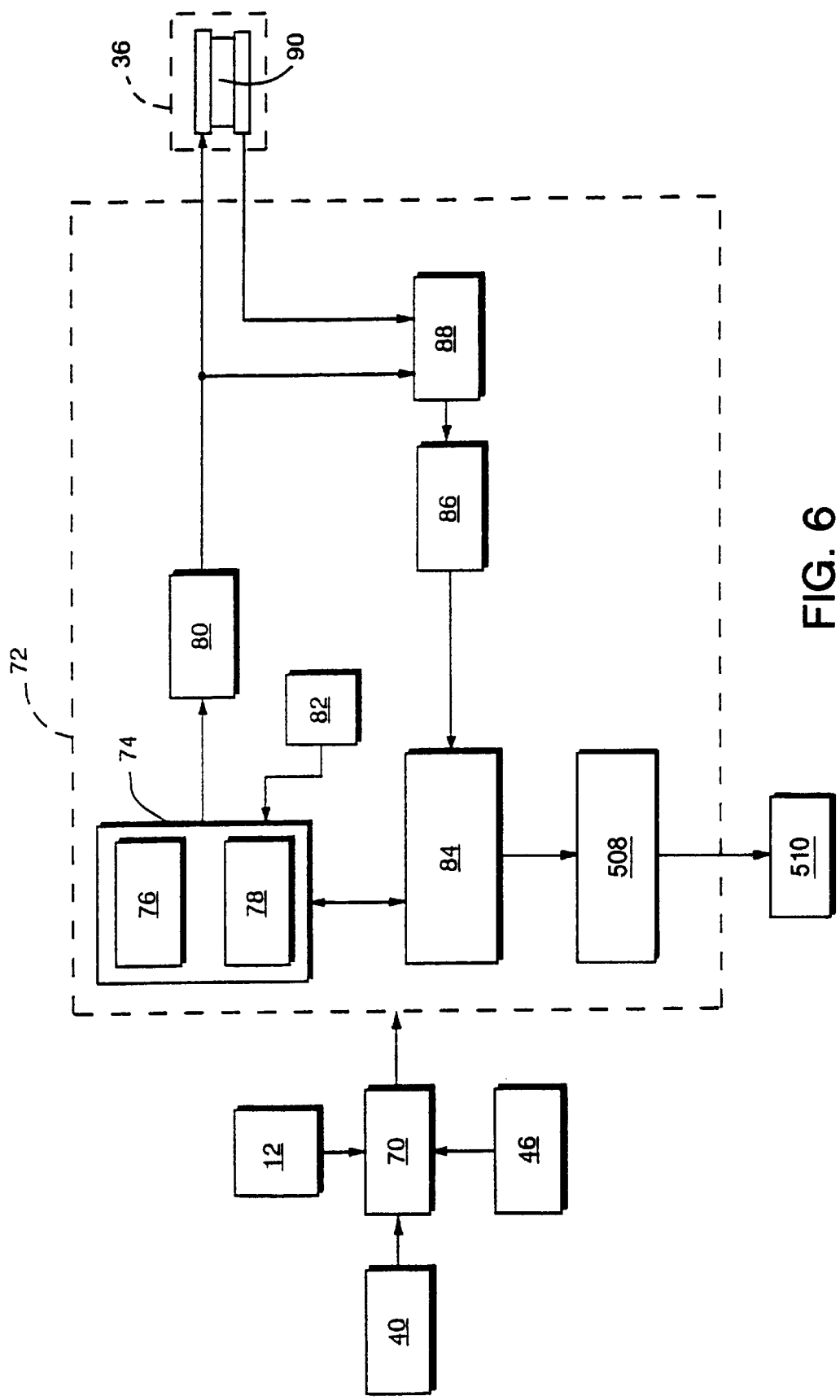
FIGS. 6–10 are function block diagrams of the vibration control system in accordance with still yet other embodiments of the invention.

FIG. 6 illustrates yet another embodiment of the invention. The FIG. 6 embodiment is similar to the FIG. 4 embodiment, except the clock 500 is replaced by an internal monitor which contains a record of inhaler use. Completing the FIG. 6 embodiment is a hatch 510 through which a physician may access, read and/or download the data from monitor 508, whereby to determine patient compliance.

Figure 7:
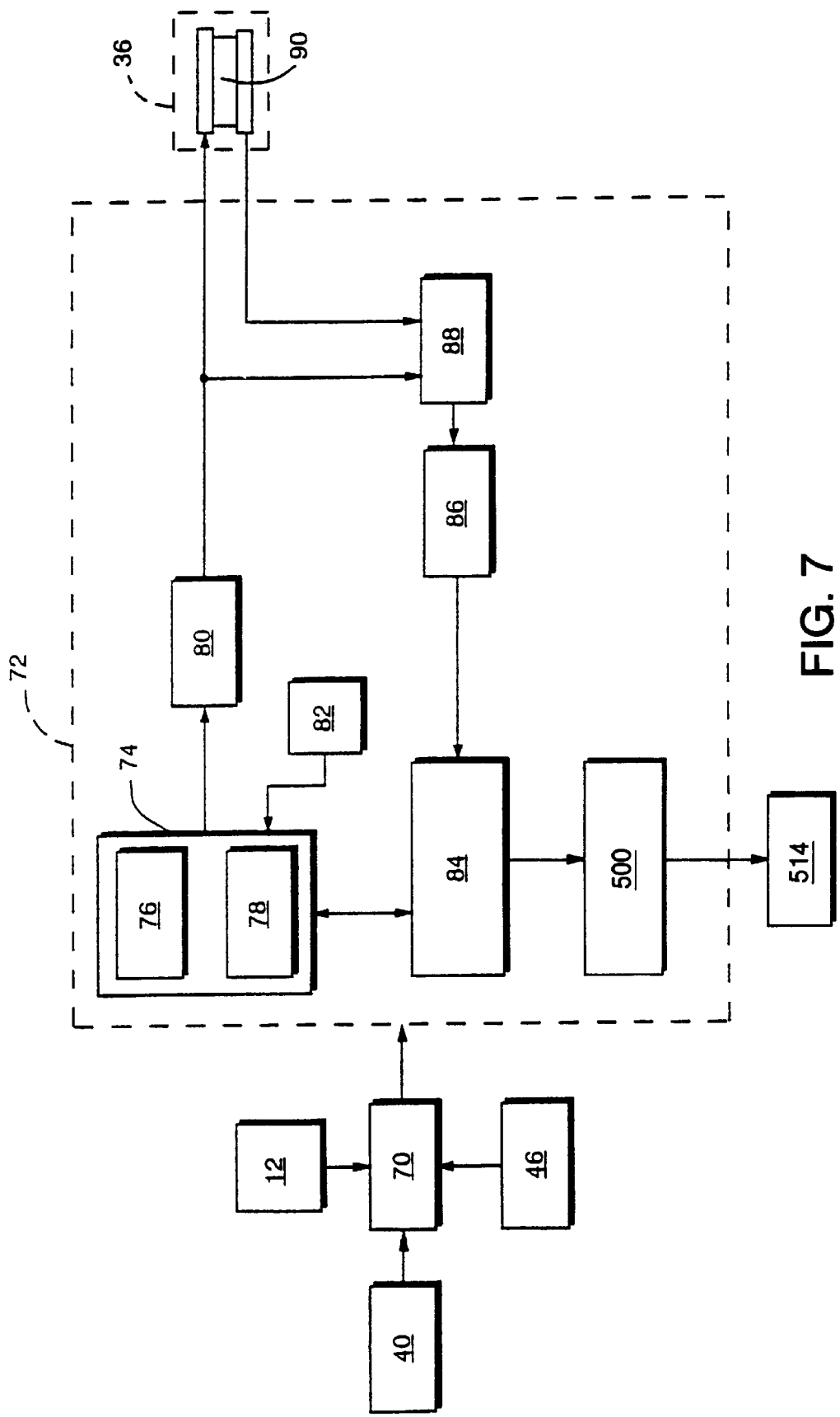

FIG. 7 illustrates yet another embodiment of the invention. The FIG. 7 embodiment is similar to the FIG. 4 embodiment except in the FIG. 7 embodiment, clock 500 counts time for the purpose of reminding a patient to use the inhaler. Thus, clock 500 is connected to a tone generator 514.

Figure 8:
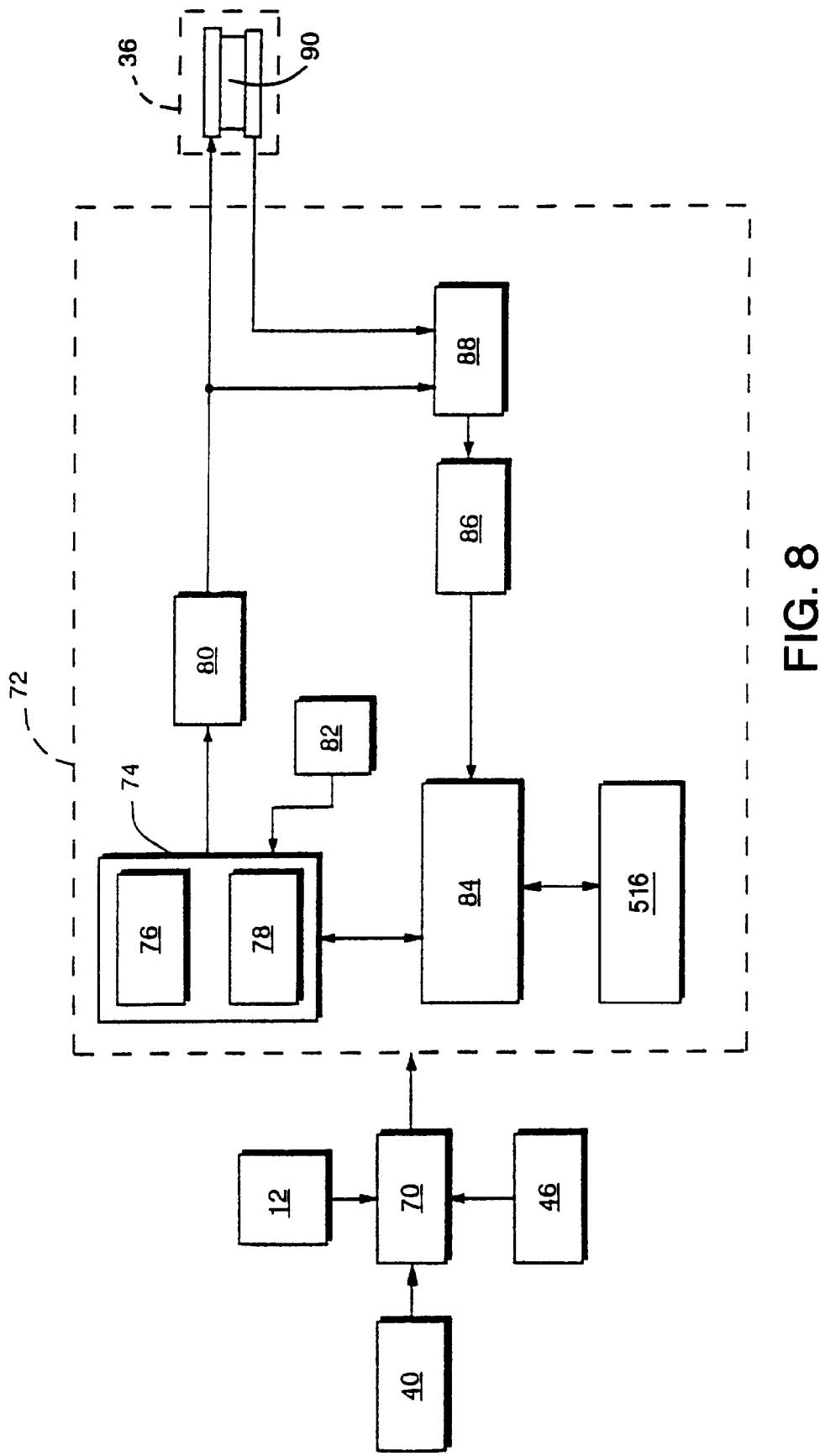

FIG. 8 illustrates yet another embodiment of the invention. The FIG. 8 embodiment is similar to the FIG. 4 embodiment, except that it includes a clock or counter 516 which sends a signal to controller 84 to alter the activation time, i.e. to a shorter or longer period, whereby to alter the quantity of drug delivered, e.g. to increase or decrease dosage over time. Alternatively, clock 516 may be programmed to disable the inhaler once a certain date is passed, i.e. so as to avoid possible use of out-of-date drugs.

Figure 9:
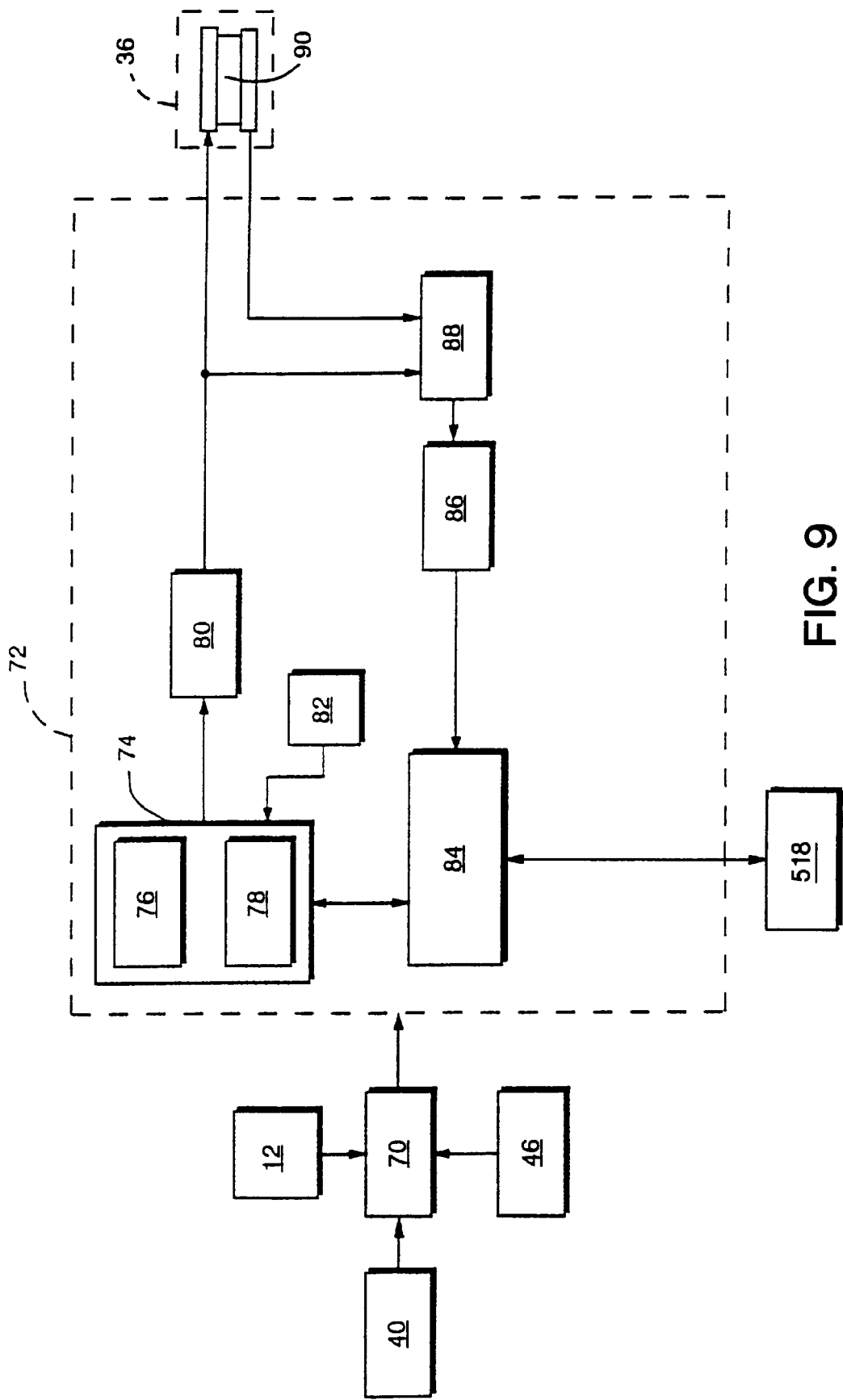

FIG. 9 illustrates yet another embodiment of the invention. FIG. 9 is similar to FIG. 4, except the counter or clock 500 is replaced with a temperature sensor 518. Certain medications are heat sensitive, and may be deactivated, or rendered potentially dangerous if exposed to high temperatures, for example, as might occur if the inhaler is left in an automobile on a sunny day. Temperature monitor 518 will deactivate controller 72 in the event a preset temperature is reached. If desired, monitor 518 also could include a display warning the patient that a preset temperature has been reached.

Figure 10:
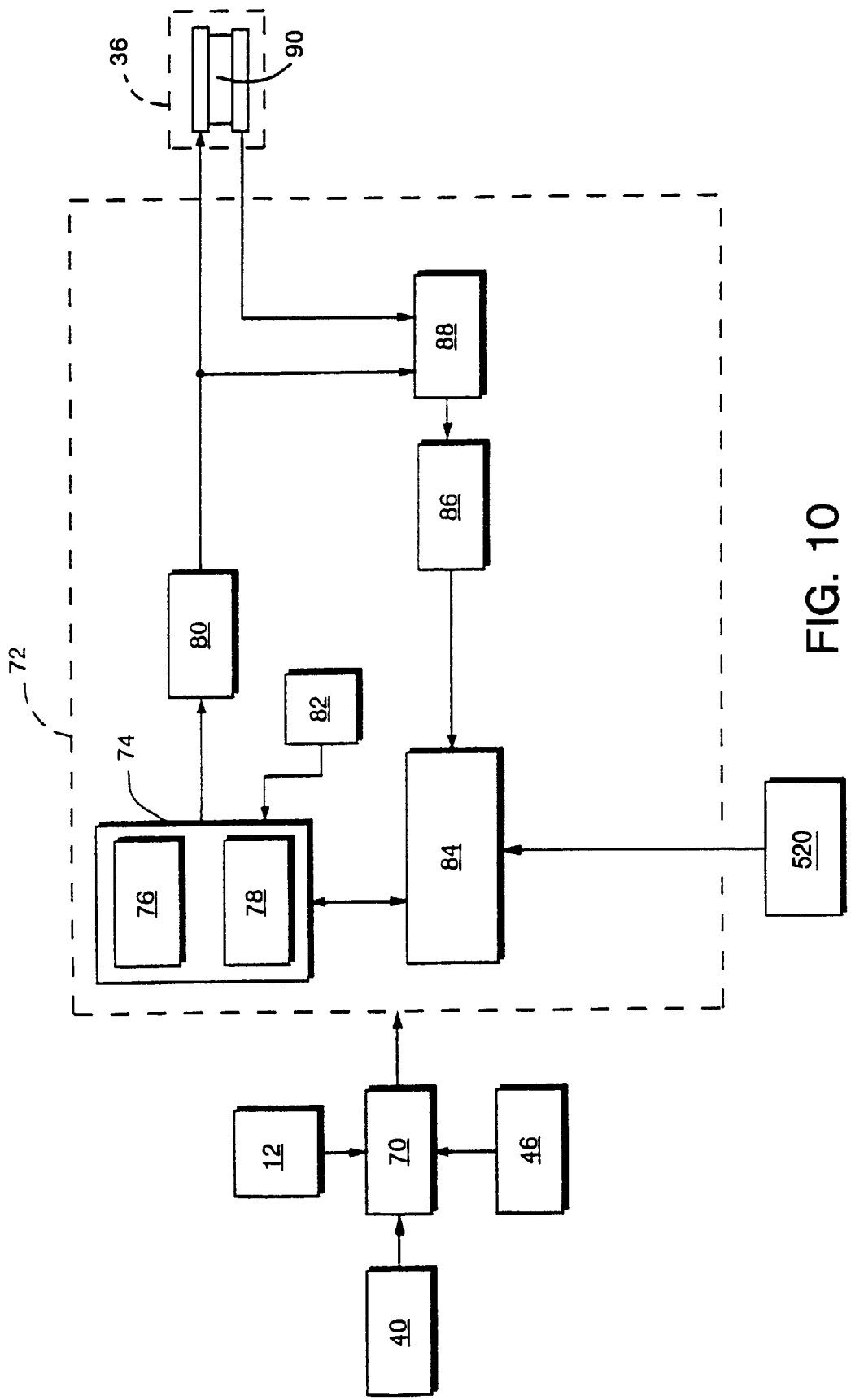

The FIG. 10 embodiment is similar to the FIG. 9 embodiment except in the FIG. 10 embodiment, the temperature sensor is replaced with a "key" such as, for example, a three button keyboard by which the user's pin code must be entered in order to activate the device. This will prevent, for example, use of the inhaler by someone other than the intended patient, and would prevent, for example, controlled or dangerous drugs from being used by children. For ease of use, key 520 may permit the patient (or druggist) to program a specific pin code for the intended user.

Figure 11:
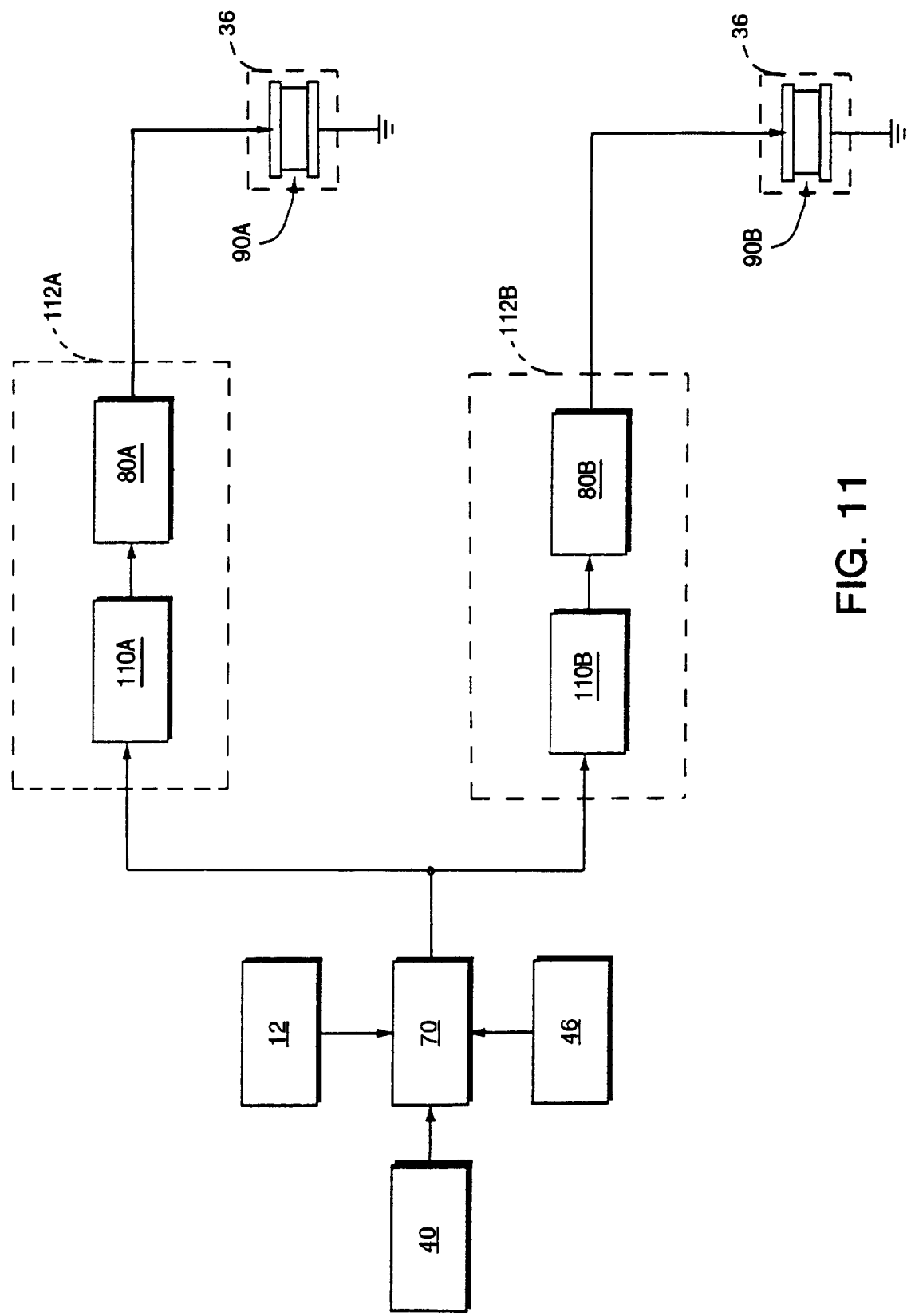
FIG. 11 is a view, similar to FIG. 3 of yet another embodiment of the invention.

Referring to FIG. 11, which illustrates yet another embodiment of the invention, in which two piezoelectric vibrators 90A, 90B, are located side-by-side within the inhaler shell. In this embodiment, piezoelectric elements 90 are designed to vibrate at different amplitudes and frequencies, i.e. so that, for example, two different drugs advantageously may be dispersed simultaneously from the same inhaler, without compromising performance or either drug. This,, permits delivery of two drugs which, while active together, may not readily be stored together. For example, an asthma inhaler may be provided containing both a bronchodilator, such as albuterol, and a steroid which may require different peizo settings. The FIG. 11 embodiment includes a pre-calibrated controller 112 which includes a first and a second pre-calibrated frequency/amplitude control signal generator 110A, 110B, which supplies control signals to pump circuit A and pump circuit B, respectively. Of course, the pre-calibrated controller 112 may be replaced with a pair of feedback controllers similar to that shown in FIG. 4.

It will be appreciated that although the foregoing detailed description proceeded with reference being made to the preferred embodiments and methods of use, the present invention is not intended to be limited to these preferred embodiments and methods of use. Rather, the present invention is of broad scope and is intended to be limited only as set forth in the accompanying claims.

What is claimed is:

1. In a dry powder inhaler comprising a first chamber, a vibrator operatively connected to said first chamber in which a dry powder is deaggregated by said vibrator and separated by size, and a second chamber in which the size-separated deaggregated powder is picked up by an air stream generated during inhalation by a patient through an opening in said inhaler and is carried for introduction into the patient, the improvement which comprises electronic circuitry with feedback control for controlling dosing.

2. In a dry powder inhaler according to claim 1, wherein said electronic circuitry includes a microprocessor controller for controlling dosing according to a pre-determined delivery protocol.

3. In a dry powder inhaler according to claim 1, the improvement wherein said electronic circuitry includes a microprocessor controller for controlling the quantity of said powder delivered over time.

4. In a dry powder inhaler according to claim 3, wherein the quantity of said powder delivered over time is varied with time.

5. In a dry powder inhaler according to claim 1, in which said electronic circuitry counts doses delivered.

6. In a dry powder inhaler according to claim 1, in which said electronic circuitry monitors patient compliance.

7. In a dry powder inhaler according to claim 6, and further including means for recording patient usage, and for downloading the resulting record to a remote reader.

8. In a dry powder inhaler according to claim 1, wherein said electronic circuitry includes a clock.

9. In a dry powder inhaler according to claim 8, and furthermore including means associated with said clock for reminding a patient.

10. In a dry powder inhaler according to claim 9, wherein said means for reminding comprises a tone generator.

11. In a dry powder inhaler according to claim 8, and further comprising a lockout device associated with said clock for limiting frequency of use of said inhaler.

12. In a dry powder inhaler according to claim 1, and further comprising a lockout device for preventing unauthorized use of said inhaler.

13. In a dry powder inhaler according to claim 1, and further comprising an environmental sensor associated with said electronic circuitry for deactivating the inhaler in the event the inhaler is exposed to ambient temperature conditions outside a predetermined range.

14. In a dry powder inhaler according to claim 13, and further comprising a display warning activated by said environmental sensor when said inhaler is exposed to ambient temperature conditions outside said predetermined range.

15. In a dry powder inhaler according to claim 1, further comprising a clock and lockout device for deactivating said inhaler at the expiration of a predetermined shelf life.

16. In a dry powder inhaler according to claim 1, wherein said electronic circuitry includes a controller for controlling operation of said vibrator over a plurality of frequencies.

17. In a dry powder inhaler according to claim 1, wherein said electronic circuitry comprises a microprocessor.

18. In a dry powder inhaler according to claim 1, wherein said electronic circuitry comprises a custom integrated circuit.

19. In a dry powder inhaler according to claim 1, wherein said electronic circuitry comprises discrete electrical and electronic components.

20. In a dry powder inhaler comprising a first chamber, a vibrator operatively connected to said first chamber in which a dry powder is deaggregated by said vibrator and separated by size, and a second chamber in which the size-separated deaggregated powder is picked up by an air stream generated during inhalation by a patient through an opening in said inhaler and is carried for introduction into the patient, the improvement wherein said first chamber contains two or more vibrators designed to vibrate at different frequencies.

21. In a dry powder inhaler comprising a first chamber, a vibrator operatively connected to said first chamber in which a dry powder is deaggregated by said vibrator and separated by size, and a second chamber in which the size-separated deaggregated powder is picked up by an air stream generated during inhalation by a patient through an opening in said inhaler and is carried for introduction into the patient, the improvement which comprises electronic circuitry for controlling dosing, and an environmental sensor associated with said electronic circuitry, for deactivating the inhaler in the event the inhaler is exposed to ambient temperature conditions outside of a predetermined range.

22. In a dry powder inhaler according to claim 21, wherein said electronic circuitry includes a microprocessor controller for controlling dosing according to a pre-determined delivery protocol.

23. In a dry powder inhaler according to claim 21, the improvement wherein said electronic circuitry includes a microprocessor controller for controlling the quantity of said powder delivered over time.

24. In a dry powder inhaler according to claim 23, wherein the quantity of said powder delivered over time is varied with time.

25. In a dry powder inhaler according to claim 21, in which said electronic circuitry counts doses delivered.

26. In a dry powder inhaler according to claim 21, in which said electronic circuitry monitors patient compliance.

27. In a dry powder inhaler according to claim 26, and further including means for recording patient usage, and for downloading the resulting record to a remote reader.

28. In a dry powder inhaler according to claim 21, wherein said electronic circuitry includes a clock.

29. In a dry powder inhaler according to claim 28, and furthermore including means associated with said clock for reminding a patient.

30. In a dry powder inhaler according to claim 29, wherein said means for reminding comprises a tone generator.

31. In a dry powder inhaler according to claim 28, and further comprising a lockout device associated with said clock for limiting frequency of use of said inhaler.

32. In a dry powder inhaler according to claim 21, and further comprising a lockout device for preventing unauthorized use of said inhaler.

33. In a dry powder inhaler according to claim 21, and further comprising a display warning activated by said environmental sensor when said inhaler is exposed to ambient temperature conditions outside said predetermined range.

34. In a dry powder inhaler according to claim 21, further comprising a clock and lockout device for deactivating said inhaler at the expiration of a predetermined shelf life.

35. In a dry powder inhaler according to claim 21, wherein said electronic circuitry includes a controller for controlling operation of said vibrator over a plurality of frequencies.

36. In a dry powder inhaler according to claim 21, wherein said electronic circuitry comprises a microprocessor.

37. In a dry powder inhaler according to claim 21, wherein said electronic circuitry comprises a custom integrated circuit.

38. In a dry powder inhaler according to claim 21, wherein said electronic circuitry comprises discrete electrical and electronic components.

39. In a dry powder inhaler comprising a first chamber, a vibrator operatively connected to said first chamber in which a dry powder is deaggregated by said vibrator and separated by size, and a second chamber in which the size-separated deaggregated powder is picked up by an air stream generated during inhalation by a patient through an opening in said inhaler and is carried for introduction into the patient, the improvement which comprises electronic circuitry for controlling dosing, said electronic circuitry including a controller for controlling operation of said vibrator over a plurality of frequencies.

40. In a dry powder inhaler according to claim 39, wherein said electronic circuitry includes a microprocessor controller for controlling dosing according to a predetermined delivery protocol.

41. In a dry powder inhaler according to claim 39, the improvement wherein said electronic circuitry includes a microprocessor controller for controlling the quantity of said powder delivered over time.

42. In a dry powder inhaler according to claim 41, wherein the quantity of said powder delivered over time is varied with time.

43. In a dry powder inhaler according to claim 39, in which said electronic circuitry counts doses delivered.

44. In a dry powder inhaler according to claim 39, in which said electronic circuitry monitors patient compliance.

45. In a dry powder inhaler according to claim 44, and further including means for recording patient usage, and for downloading the resulting record to a remote reader.

46. In a dry powder inhaler according to claim 39, wherein said electronic circuitry includes a clock.

47. In a dry powder inhaler according to claim 46, and furthermore including means associated with said clock for reminding a patient.

48. In a dry powder inhaler according to claim 47, wherein said means for reminding comprises a tone generator.

49. In a dry powder inhaler according to claim 46, and further comprising a lockout device associated with said clock for limiting frequency of use of said inhaler.

50. In a dry powder inhaler according to claim 39, and further comprising a lockout device for preventing unauthorized use of said inhaler.

51. In a dry powder inhaler according to claim 39, further comprising a clock and lockout device for deactivating said inhaler at the expiration of a predetermined shelf life.

52. In a dry powder inhaler according to claim 39, wherein said electronic circuitry comprises a microprocessor.

53. In a dry powder inhaler according to claim 39, wherein said electronic circuitry comprises a custom integrated circuit.

54. In a dry powder inhaler according to claim 39, wherein said electronic circuitry comprises discrete electrical and electronic components.

\* \* \* \* \*